United States Patent
Schläpfer

[11] Patent Number: 6,117,135
[45] Date of Patent: Sep. 12, 2000

[54] DEVICE FOR BONE SURGERY

[75] Inventor: Fridolin Schläpfer, Glarus, Switzerland

[73] Assignee: Synthes (U.S.A.), Paoli, Pa.

[21] Appl. No.: 09/214,688

[22] PCT Filed: Jul. 9, 1996

[86] PCT No.: PCT/CH96/00254
§ 371 Date: Jan. 8, 1999
§ 102(e) Date: Jan. 8, 1999

[87] PCT Pub. No.: WO98/01076
PCT Pub. Date: Jan. 15, 1998

[51] Int. Cl.[7] .................................... A61B 17/70
[52] U.S. Cl. ........................ 606/61; 606/69; 606/73
[58] Field of Search ........................ 606/61, 64, 60, 606/72, 73; 623/17

[56] References Cited

U.S. PATENT DOCUMENTS

| | | | |
|---|---|---|---|
| 4,289,123 | 9/1981 | Dunn | 606/61 |
| 5,569,251 | 10/1996 | Baker et al. | 606/73 |
| 5,620,443 | 4/1997 | Gertzbein et al. | 606/61 |
| 5,800,433 | 9/1998 | Benzel et al. | 606/61 |
| 5,843,082 | 12/1998 | Yuan et al. | 606/61 |
| 5,928,232 | 7/1999 | Howland et al. | 606/61 |
| 5,954,722 | 9/1999 | Bono | 606/61 |

*Primary Examiner*—Gene Mancene
*Assistant Examiner*—Pedro Philogene
*Attorney, Agent, or Firm*—Pennie & Edmonds LLP

[57] ABSTRACT

The invention relates to a device for bone surgery which has the shape of a plate-shaped jaw (30) with a lower surface (1), an upper surface (2), a right long side (3), a left long side (4), a front surface (5) and a rear surface (6) and at least two holes (7, 8) which are intended to hold bone screws and extend from the upper surface (2) to the lower surface (1), and bore through the jaw (30). Said jaw (30) also has a right bore (9) intended to hold a right longitudinal member (11) and having a longitudinal axis (15), said bore connecting the front surface (5) to the rear surface (6) and extending adjacent the right longitudinal surface (3). Said jaw also has a left bore (10) intended for holding a left longitudinal member (12) and having a longitudinal axis (16) which connects the front surface (5) to the rear surface (6) and extends adjacent to the left long side (4) and parallel to the right bore (9). Moreover, the lower surface (1) of the jaw (3) has a concave shape.

35 Claims, 3 Drawing Sheets

DEVICE FOR BONE SURGERY

FIELD OF THE INVENTION

The present invention relates to a fixation device for bone surgery including a plate-shaped jaw member configured to permit the use of longitudinal members without undue increase in thickness of the plate-shaped jaw member.

BACKGROUND OF THE INVENTION

Anterior fixations in the area of the spinal column have been achieved with plate-shaped devices, as shown in WO94/17744, for example. Such plate-shaped devices have the great advantage of having very limited thickness (between 1.1 and 2.0 mm), and thus are only slightly invasive.

A drawback of such plate-shaped devices, however, is that the fusion zone of the affected vertebrae cannot be actively placed under pressure, which can lead to instances of pseudo-arthrosis. A further drawback is the great variety of the necessary assortment of instruments with greatly varying dimensions that are available to the surgeon. Typically, depending on the manufacturer, 12 to 23 plate types are required.

Devices with longitudinal members, as used in posterior fixation in the area of the spinal cord, have not been able to be used in clinical practice on account of their considerable thickness imposed by design limitations. However, longitudinal members have the advantage of permitting the application of active compression to the treatment site, and would require only a minimum assortment of instruments.

SUMMARY OF THE INVENTION

In accordance with the principle of the present invention, a device for bone surgery is provided which permits an anterior fixation in the area of the spinal cord and which combines the advantages of plate-shaped devices (having limited thickness) with devices including longitudinal members (which permit the application of active compression).

The device of the present invention has a plate-shaped jaw member with a concave lower surface which rests on the vertebra. Longitudinal members may be positioned through bores extending along the long sides of the plate-shaped device. The seating of the longitudinal members through the plate-shaped device requires a greater thickness of the device according to the diameter of the longitudinal members. However, the concavity of the lower side of the plate-shaped device permits a flat shape of the plate-shaped device in the central area (between the bores through which the longitudinal members are positioned) because the longitudinal members are laterally situated at positions where the thickness of the device is greater due to the concavity of the lower side of the device. Due to the concavity, the longitudinal members laterally situated within the plate-shaped jaw member scarcely contribute to the thickness of the plate-shaped jaw member within the central area of the device (area of the esophagus), in which the bone screws are used, hardly increase its thickness. In this area the thickness of the plate-shaped jaw member can be limited to 2 mm.

The thickness of the plate can be kept limited (about 5 mm) even if fastening screws are used to fix the longitudinal members, thanks to the arrangement of the fastening screws at an acute angle with respect to a plane extending between the longitudinal axes of the longitudinal members. The thickness of the plate-shaped device can even be further reduced if longitudinal members with a reduced diameter are used.

The geometry of the body of a cervical vertebra makes it possible to position the longitudinal members laterally in relation to the front longitudinal fastener so far posterior, that the device according to the invention exhibits a similar thickness toward the front longitudinal fastener, in the area of the esophagus, as a conventional plate. Only in the area of the musculus longus colli, where it is less critical, is the thickness of the device determined by the diameter of the longitudinal members. The lateral arrangement of the longitudinal members also contributes to the stability and firmness of the rotation of the fixation device.

In a preferred embodiment, the fixation device of the present invention includes two plate-shaped jaws and two longitudinal members. Two bone screws and two fastening screws preferably are provided for each plate-shaped jaw. Preferably, the fastening screws for fastening the longitudinal members run at an angle α with respect to the plate surface of the jaw. Additionally, the fastening screws preferably have external threading and are designed such that the part of the fastening screw that protrudes from the jaw, with a given movement of tightening, is twisted off at a predetermined breaking point, so that after fixation has been achieved, no remaining parts of the fastening screw extends from the plate-shaped jaw.

These and other features and advantages of the present invention will be readily apparent from the following detailed description of the invention, the scope of the invention being set out in the appended claims.

BRIEF DESCRIPTION OF THE DRAWINGS

The detailed description will be better understood in conjunction with the accompanying drawings, wherein like reference characters represent like elements, as follows.

DETAILED DESCRIPTION OF THE INVENTION

Figure 1:
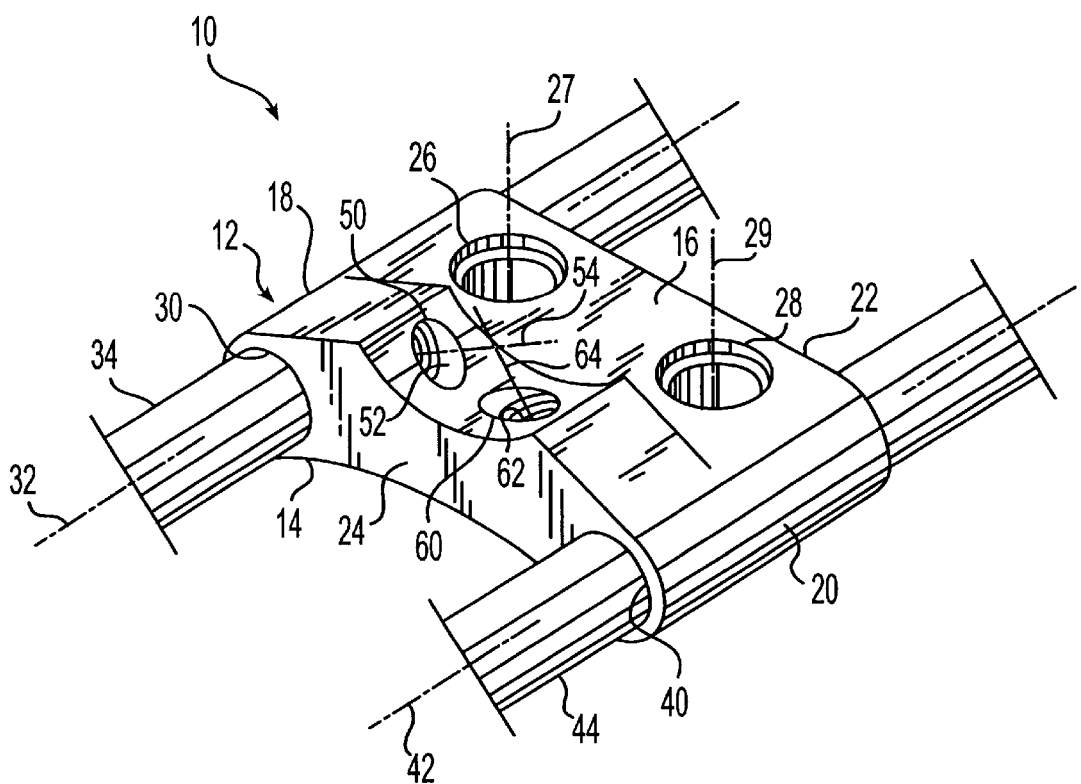
FIG. 1 is a perspective view of a bone surgery device formed in accordance with the principles of the present invention with longitudinal members inserted.

A fixation device 10 for bone surgery formed in accordance with the principles of the present invention is shown in FIGS. 1 to 4. Fixation device 10 includes a plate-shaped member 12 (hereinafter designated as "jaw 12" for short) having a lower surface 14, an upper surface 16, a right long side 18, a left long side 20, a front surface 22, and a rear surface 24. Preferably, lower surface 14 is concave.

Two holes 26, 28, configured to hold bone screws, extend from upper surface 16 to lower surface 14 and bore through jaw 12. Preferably, axes 27, 29 of respective holes 26, 28 are at an angle with respect to upper surface 16, as described in further detail below.

Jaw 12 further includes a right longitudinal bore 30 having a longitudinal axis 32 and configured to hold a right longitudinal member 34. Right longitudinal bore 30 connects front surface 22 with rear surface 24 and runs in the vicinity of right long side 18. In a symmetrical position in relation to right longitudinal bore 30 and right long side 18, jaw 12 also includes a left longitudinal bore 40 having a longitudinal axis 42 and configured to hold a left longitudinal member 44. Left longitudinal bore 40 connects front surface 22 with rear surface 24 and runs in the vicinity of left long side 20. Longitudinal bores 30, 40 run parallel to each other and at as great a distance as possible from each other in the lateral areas of jaw 12. Longitudinal bores 30, 40 straddle holes 26, 28 such that fixation of jaw 12 is accomplished at a location between bores 30, 40. Longitudinal members 34, 44 may have an external surface provided with threading, such as asymmetrical threading, or a smooth external surface.

Figure 2:
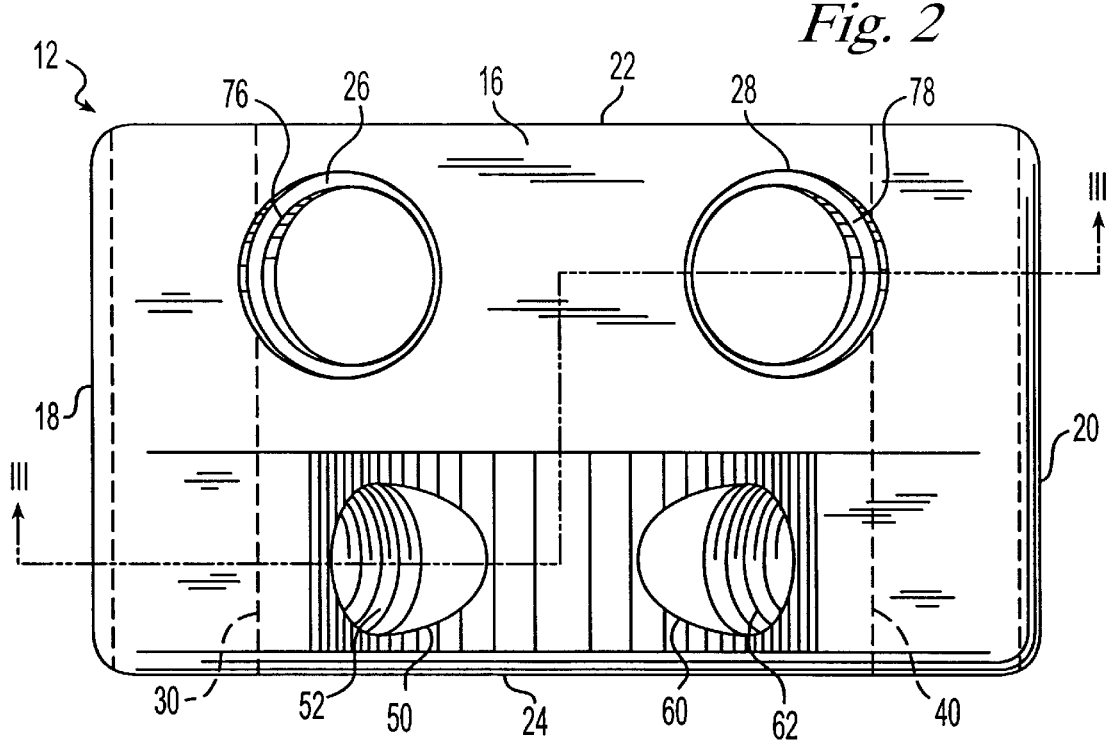
FIG. 2 is a top elevational view of the bone-surgery device of FIG. 1.
Figure 3:
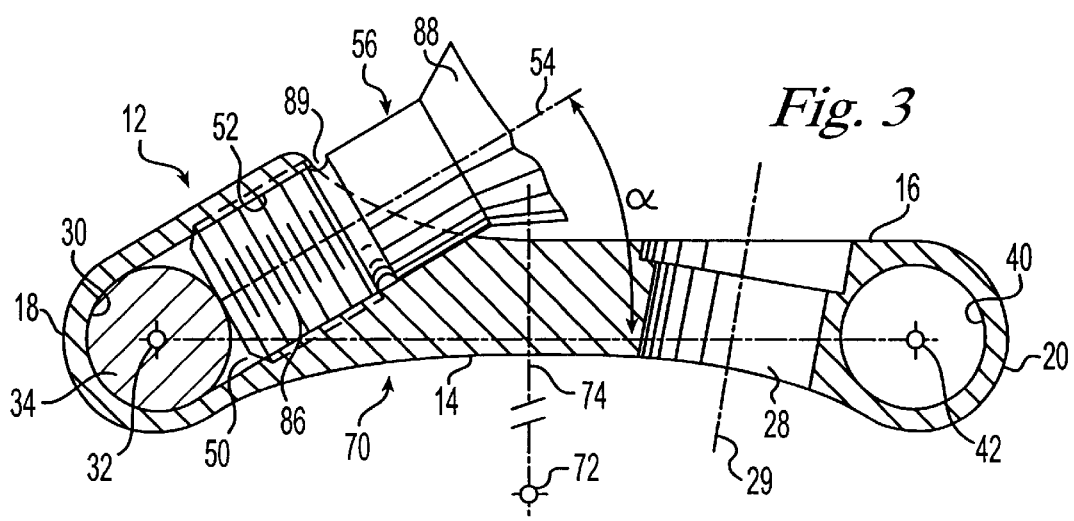
FIG. 3 is a cross-sectional view along line III—III of FIG. 2.
Figure 4:
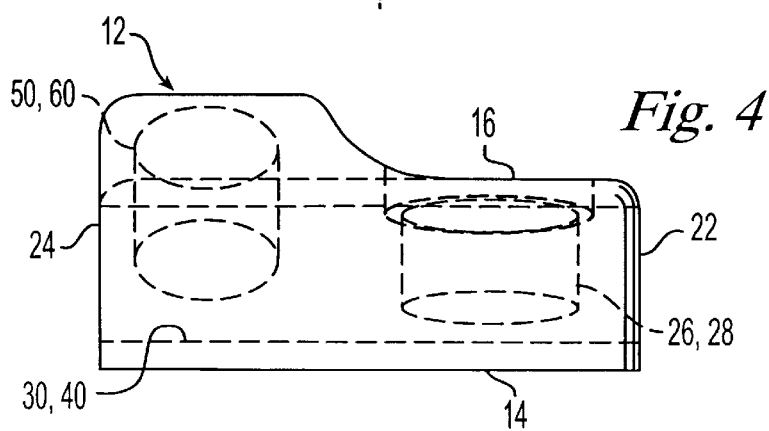
FIG. 4 is a side elevational view of the bone-surgery device of FIG. 1.

In a preferred embodiment, jaw 12 additionally includes a right opening 50 with internal threading 52 and a longitudinal axis 54, as shown in FIG. 2. Right opening 50 connects upper surface 16 with right bore 30. Right opening 50 is configured to hold a right fastening screw 56, as shown in FIG. 3, which extends therethrough to contact and fix right longitudinal member 34 as desired. Symmetrically positioned in relation to right opening 50 is a left opening 60 with internal threading 62 and longitudinal axis 64. Left opening 60 connects upper surface 16 with left longitudinal bore 40. Left opening 60 is configured to hold a left fastening screw similar to right fastening screw 56 which extends therethrough to contact and fix left longitudinal member 44 as desired.

As discussed above, lower surface 14 of jaw 12 is concave. As can be seen from FIG. 3, lower surface 14 preferably forms a cylindrical segment 70 with a radius of curvature of between approximately 12.5 and 30 mm, preferably between approximately 20 and 27 mm. Longitudinal axis 72 of cylindrical segment 70 preferably runs parallel to longitudinal axes 32, 42. Preferably, lower surface 14 is comprised of several cylindrical segments that merge into one another. Preferably, the radius of curvature of lower surface 14 is between approximately 20 and 30 mm in the area of the central axis 74 and between approximately 10 and 15 mm in the lateral area directed against longitudinal axes 32,42 of bores 30, 40, respectively. Central axis 74 of jaw 12 is preferably perpendicular to plane P extending between longitudinal axes 32, 42.

Holes 26, 28 preferably include threading 76, 78, respectively, which advantageously exhibit the same ascending gradient as the outside threading 80 of bone screw 82 (FIG. 5) inserted therethrough. However, alternative connections between jaw 12 and bone screw 82 may be used instead. For example, a spherical hole 84 (FIG. 5) may be provided to hold a bone screw with a spherical head, which allows for a swiveling area for the axis of the bone screw. Alternatively, a circular cylindrical hole for holding a bone screw with an adjusting head may be provided. Yet another option is to provide a cone-shaped hole for automatically locking and holding a bone screw with a corresponding cone-shaped head.

Axes 27, 29 of respective holes 26, 28 are positioned in a plane which is perpendicular to longitudinal axes 34, 44 of longitudinal members 30, 40, as may be appreciated with reference to FIG. 3. Axes 27, 29 preferably are at an angle of between approximately 5° and 13°, preferably between approximately 7° and 9°, with respect to central axis 74. Preferably, axes 27, 29 converge toward lower surface 14 and thus the bone to be treated. However, in certain cases, for example with osteoporotic bones, a diverging arrangement of holes 26, 28 (5° to 12°, preferably 8° to 10°, measured from central axis 66) is advantageous. Both the converging and diverging arrangements of holes 26, 28 have associated advantages. With the converging arrangement there is a lesser danger of injuring the blood vessels that run alongside the vertebrae. The diverging arrangement is particularly advantageous in the case of osteoporotic bones because of the better consistency of the bones against the edge of the body of the vertebra.

In certain applications, for example in anchoring in the upper cervical or the lower cervical region, it is advantageous if the axes 27, 29 of holes 26, 28 are not positioned in a plane which is perpendicular to longitudinal axes 32, 42. Instead, in such applications, axes 27, 29 preferably encompass an angle of approximately 5° to 15°, preferably of approximately 10° to 12°, with respect to a plane perpendicular to longitudinal axes 32, 42 and are directed toward front surface 22.

Respective longitudinal axes 54, 64 of openings 50, 60 are oriented at an acute angle α with respect to plane P extending between longitudinal axes 32, 42 of bores 30, 40, as may be appreciated with reference to FIG. 3. Angle α preferably is in the range of between approximately 15° and 35°, and preferably between approximately 20° and 30°. Axes 54, 64 preferably converge toward upper surface 16 of jaw 12 so that openings 50, 60 take up as little space as possible.

Fastening screw 56 is screwed into right opening 50. Preferably, fastening screw 56 has external threading 86 corresponding to threading 52 of opening 50. Fastening screw 56 is provided to fix right longitudinal member 34 longitudinally while permitting longitudinal member 34 to rotate. When a defined tightening movement is made, head 88 of fastening screw 56 is twisted off at the pre-determined breaking point 89, so that after fixation has been achieved, no remaining parts of fastening screw 56 are present extending above upper surface 16 of jaw 12. In an analogous manner, a similar fastening screw 56 can be screwed into left opening 60 with threading 62. Head 88 of fastening screw 56 can be equipped with a hexagon socket, torx or hexagon insert bit.

It will be appreciated that different methods of fixing longitudinal members 34, 44 may be used, instead. For example, instead of using a fastening screw 56, longitudinal members 34, 44 may be clamped in bores 30, 40 from the side with the help of tongs, by pressing in bores 30, 40 from the side. The clamping may be enhanced, if instead of using longitudinal members 34, 44 with a solid profile, tubes with the same outside diameter are used. Alternatively, longitudinal members with an outside thread and nuts may be used. Yet another alternative is to slide conical, slotted sleeves onto longitudinal members 34, 44. Such sleeves preferably have a slightly greater diameter than bores 30, 40 for longitudinal members 34, 44. By the sleeves being pressed into bores 34, 44, longitudinal members 34, 44 are clamped.

Figure 5:
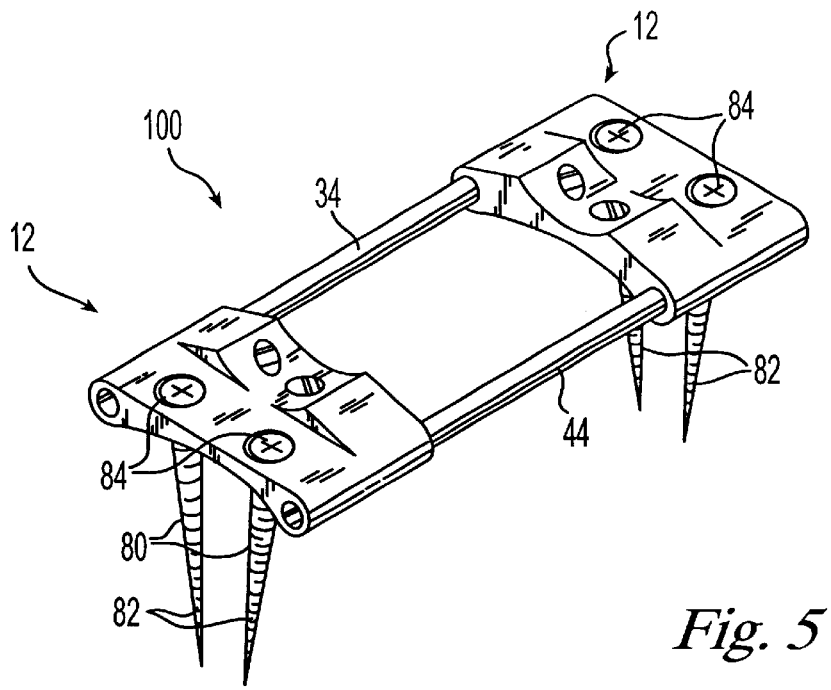
FIG. 5 is a perspective view of a bone surgery device formed in accordance with the principles of the present invention with two plate-shaped jaws as shown in FIG. 1.

A bone surgery device 100 with two jaws 12, each corresponding to jaw 12 of bone surgery device 10 of FIGS. 1–4, is shown in FIG. 5. Fixation device 100 includes two longitudinal members 34, 44 and four bones screws 82, the use of which is described in detail below. In this construction, the pair of bone screws 82 of each jaw 12 preferably converge as screws 82 extend away from jaw 12 and into the bone.

Figure 6:
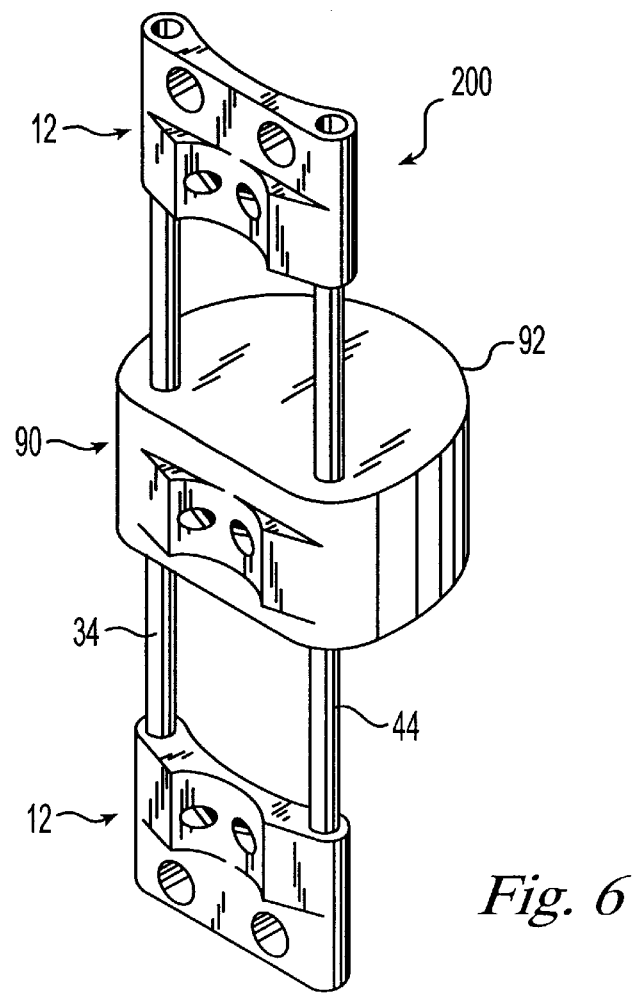
FIG. 6 is a perspective view of the fixation device of the present invention with two plate-shaped jaws as shown in FIG. 1 and with a replacement body of a vertebra located between the two plate-shaped jaws.

A variant 200 of fixation device 100 of FIG. 5 is shown in FIG. 6, as applied in tumor resections. In tumor resections, whole bodies of vertebrae must be replaced. In such situations, a vertebra replacement 90 that can be connected with longitudinal members 34, 44, integrated into fixation device 200 according to the invention, can be used. Vertebra replacement 90 is designed in an anterior manner, like the plate-shaped jaws 12 according to the invention, and can thus be pushed onto both longitudinal members 34, 44. At the posterior, vertebra replacement 90 is comprised of one block 92 which fills the intervertebral space. The entire construction of fixation device 200 of FIG. 6 is thus comprised of two jaws 12, two longitudinal members 34, 44, and vertebra replacement 90 located between the two jaws 12. Thanks to the rod construction, the vertebra replacement 90 can be placed under compression.

The operation technique of the fixation device 100 or 200 of FIGS. 5 and 6, respectively, is described below in detail and includes the following steps.

First, a pair of longitudinal members 34, 44 and pair of plate-shaped jaws 12 are selected. Each jaw 12 is then equipped with one of longitudinal members 34, 44. Longitudinal members 34, 44 must be applied in a complementary manner. This is achieved by arranging both jaws 12 on a table in such a way that holes 26, 28 for the bone screws 82 (as seen from the viewer's perspective) are located above. A longitudinal member 34, 44 is inserted into the left bore 40 of each jaw 12.

Each longitudinal members 34, 44 is then fixed within its respective left bore 40 by means of a corresponding fastening screw 56. Heads 88 of fastening screw 56 are twisted off at their pre-determined breaking point 89. Because of this arrangement, only two more attachment screws 56, located diagonally to one another, need to be operated in situ, as will be appreciated.

The pair of rod constructions, each including one jaw 12 with a corresponding longitudinal member 34 or 44 inserted in left bore 40 of jaw 12, may then be assembled by inserting the free end of each longitudinal member 34, 44, (the other end of which is already inserted within the left bore 40 of one jaw 12) into the right bore 30 of the other jaw 12. The fastening screw 56 for each of the newly inserted longitudinal members 34, 44 is slightly turned without twisting off heads 88 thereof. It will be appreciated that the newly inserted fastening screws 56 are positioned diagonally across from each other because the right bores 30 into which a longitudinal member 34, 44 and corresponding fastening screw 56 have been inserted are diagonally across from each other as shown in FIG. 5.

The rod construction is then placed on the patient and fixed by means of bone screws 82. The connection of jaws 12 preferably is achieved by means of two bone screws 82 on each jaw 12. At this point, bones screws 82, depending on the arrangement of holes 26, 28, are introduced either so that they diverge or converge in order to minimize the risk of bone screws 82 being pulled out.

As necessary, the bone chip or the vertebra replacement is compressed by way of the rod construction. The two remaining fastening screws 56 are then tightened by twisting off their respective head 88 at the pre-determined breaking point. For this purpose, a 90° offset ring wrench is pushed over each fastening screw 56. Thanks to the special position of the two longitudinal members 34, 44 described above, the fastening screws 56 that are to be tightening in situ are firmly tightened, by turning the fastening screws 56 outward and away from one another. It is thereby possible to tighten both fastening screws 56 at the same time, without the two instruments getting into the way of one another, and without the tightening movement being countered during tightening. In certain situations, it is desirable to additionally fix the bone chip. With an additional jaw with a hole in the middle, this requirement can also be met.

While the foregoing description and drawings represent the preferred embodiments of the present invention, it will be understood that various additions and/or substitutions may be made therein without departing from the spirit and scope of the present invention as defined in the accompanying claims. One skilled in the art will appreciate that the invention may be used with many other modifications of structure, forms, arrangement, proportions, materials, and components and otherwise, used in the practice of the invention and which are particularly adapted to specific environments and operative requirements, without departing from the principles of the present invention. It will be appreciated that although the bone surgery device described herein is particularly well suited for application in the area of the cervical vertebrae, the components of the device of the present invention may be modified as desired for use in other vertebral areas as well. The presently disclosed embodiments are therefore to be considered in all respects as illustrative and not restrictive, the scope of the invention being indicated by the appended claims, and not limited to the foregoing description.

What is claimed is:

1. A bone surgery device including a plate-shaped jaw, said plate-shaped jaw comprising:
    a lower surface;
    an upper surface;
    a right long side;
    a left long side;
    a front surface;
    a rear surface;
    at least two holes each extending from said upper surface to said lower surface and configured to hold a bone screw;
    a right bore with a longitudinal axis adjacent said right long side;
    a left bore with a longitudinal axis adjacent said left long side; and
    at least two bone screws, one extending through each bone screw hole, with the bone screws being configured and dimensioned to attach the plate shaped jaw to vertebra material;
    wherein:
        said lower surface is concave;
        said right bore connects said front surface with said rear surface and is configured to hold a right longitudinal member;
        said left bore connects said front surface with said rear surface and is configured to hold a left longitudinal member;
        said longitudinal axes of said right and left bores are substantially parallel to each other; and
        said holes for said bone screws are positioned between said longitudinal axes of said right and left bores.

2. A device as in claim 1, wherein said plate-shaped jaw further comprises:
    a right opening in upper surface 16 provided with a thread and configured to hold a right fastening screw; said right opening connecting said upper surface with said right bore; and
    a left opening in upper surface 16 provided with a thread and configured to hold a left fastening screw, said left opening connecting said upper surface with said left bore.

3. A device in claim 2, wherein:
a plane is defined between said longitudinal axes of said right and left bores of said plate-shaped jaw; and
said right and left openings of said plate-shaped jaw have longitudinal axes at an angle with respect to said plane between said longitudinal axes of said right and left bores.

4. A device as in claim 3, wherein said longitudinal axes of said right and left openings of said plate-shaped jaw converge toward said upper surface of said plate-shaped jaw.

5. A device as in claim 4, wherein said longitudinal axes of said right and left openings of said plate-shaped jaw are at an angle in the range of approximately 15° to 335° with respect to said plane.

6. A device as in claim 5, wherein said longitudinal axes of said right and left openings of said plate-shaped jaw are at angle of between approximately 20° and 30° with respect to said plane.

7. A device as in claim 1, wherein said lower surface of said plate-shaped jaw forms a cylindrical segment with a cylindrical axis running parallel to said longitudinal axes of said right and left bores of said plate-shaped jaw.

8. A device as in claim 7, wherein said cylindrical segment has a radius of curvature of between approximately 12.5 and 30 mm.

9. A device as in claim 8, wherein said cylindrical segment has a radius of curvature of between approximately 20 and 27 mm.

10. A device as in claim 1, wherein:
said lower surface of said plate-shaped jaw is comprised of various cylindrical segments merging into one another,
a centrally located cylindrical segment has a radius of curvature of between 20 and 30 mm; and
laterally located cylindrical segments respectively adjacent said longitudinal axes of said right and left bores of said plate-shaped jaw have a radius of curvature of between 10 and 15 mm.

11. A device as in claim 1, wherein said bone screw holes of said plate-shaped jaw have longitudinal axes at an angle with respect to a plane perpendicular to said longitudinal axes of said right and left bores and directed toward said front surface.

12. A device as in claim 11, wherein said longitudinal axes of said bone screw holes are at an angle of between approximately 5° to 15° with respect to the plane perpendicular to said longitudinal axes of said right and left bores.

13. A device as in claim 1, wherein:
a plane is defined between said longitudinal axes of said right and left bores of said plate-shaped jaw;
a central axis is defined perpendicular to said plane;
said bone screw holes of said plate-shaped jaw have longitudinal axes at an angle with respect to said central axis; and
said longitudinal axes of said bone screw holes converge toward each other in a direction toward said lower surface.

14. A device as in claim 13, wherein said longitudinal axes of said bone screw holes are at an angle of between approximately 5° and 13° with respect to said central axis.

15. A device as in claim 14, wherein said longitudinal axes of said bone screw holes are at an angle of between approximately 7° and 9° with respect to said central vertical axis.

16. A device as in claim 1, wherein:
a plane is defined between said longitudinal axes of said right and left bores of said plate-shaped jaw;
a central axis is defined perpendicular to said plane;
said bone screws holes of said plate-shaped jaw have longitudinal axes at an angle with respect to said central axis; and
said longitudinal axes of said bone screw holes diverge from each other in a direction toward said lower surface.

17. A device as in claim 13, wherein said longitudinal axes of said bone screw holes are at an angle of between approximately 5° and 12° with respect to said central vertical axis.

18. A device as in claim 14, wherein said longitudinal axes of said bone screw holes are at an angle of between approximately 8° and 10° with respect to said central vertical axis.

19. A device as in claim 1, wherein a first plane is defined between said longitudinal axes of said right and left bores of said plate-shaped jaws, and said bone screw holes of said plate shaped jaws are internally threaded with each having a longitudinal axis that is oriented in a second plane that is perpendicular to the first plane.

20. A device as in claim 1, wherein said bone screw holes of said plate-shaped jaw exhibit a spherical counterbore in the area of said upper surface of said plate-shaped jaw to hold a spherical screw head.

21. A device as in claim 1, wherein said bone screw holes of said plate-shaped jaw are conical in shape, in order to hold a conical screw head.

22. A device as in claim 1, wherein said bone screw holes of said plate-shaped jaw have a circular cylindrical shape to hold a circular cylindrical screw head.

23. A device as in claim 1, wherein said bone screw and said bone screw holes are threaded with the same ascending gradient.

24. A device as in claim 1, further comprising right and left longitudinal members extending through said right and left bores, respectively, of said plate-shaped jaw and straddling said bone screw holes.

25. A device as in claim 24, wherein:
said plate-shaped device further comprises a right opening extending from said upper surface to said right bore and configured to receive a fastening screw, and a left opening extending from said upper surface to said left bore and configured to receive a fastening screw; and
said device further comprises a fastening screw extending through each of said right and left openings to fix said right and left longitudinal members, respectively, in a desired position.

26. A device as in claim 25, wherein each of said fastening screws has a head formed to be twisted off with a predetermined tightening movement beyond a predetermined breaking point of said head.

27. A device as in claim 24, wherein said longitudinal members are externally threaded.

28. A device as in claim 27, wherein said threading of said longitudinal members is asymmetrical.

29. A device as in claim 24, wherein said longitudinal members have a smooth external surface.

30. A device as in claim 1, further comprising a second plate-shaped jaw comprising:
a lower surface;
an upper surface;
a right long side;
a left long side;
a front surface;
a rear surface;

at least two holes each extending from said upper surface to said lower surface and configured to hold a bone screw;

a right bore with a longitudinal axis adjacent said right long side; and and a left bore with a longitudinal axis adjacent said left long side;

wherein:

said lower surface is concave;

said right bore connects said front surface with said rear surface and is configured to hold a right longitudinal member;

said left bore connects said front surface with said rear surface and is configured to hold a left longitudinal member;

said longitudinal axes of said right and left bores are substantially parallel to each other; and said holes for said bone screws are positioned between said longitudinal axes of said right and left bores.

31. A fixation device as in claim 30, further comprising four bone screws, each positioned in a respective bone screw hole in said first and second plate-shaped jaws.

32. A fixation device as in claim 30, further comprising:

a right longitudinal member extending through said right bore of said first plate-shaped jaw and said left bore of said second plate-shaped jaw;

a left longitudinal member extending through said left bore of said first plate-shaped jaw and said right bore of said second plate-shaped jaw;

a right opening extending from said upper surface to said right bore and configured to receive a fastening screw; and a left opening extending from said upper surface to said left bore and configured to receive a fastening screw.

33. A fixation device as in claim 32, further comprising a fastening screw in each of said right and left openings of said first and second plate-shaped jaw members.

34. A device as claimed in claim 1 further comprising a vertebra replacement member which includes a block having front and rear surfaces and at least two holes configured to receive the right and left longitudinal members, with the front surface of the block being spaced from the rear surface of said plate shaped jaw along said longitudinal members.

35. A device as claimed in claim 34 further comprising a second, identically configured plate shaped jaw on said longitudinal members and spaced from the rear surface of the block.

* * * * *